United States Patent [19]

Leftwick et al.

[11] 4,347,252

[45] Aug. 31, 1982

[54] RODENTICIDAL 1-(3,5-BISTRIFLUOROMETHYLPHENYL)-3-(4-T-BUTYLPIPERIDINO)PROP-1-YNE

[75] Inventors: Allan P. Leftwick, Ilford; Edgar W. Parnell, Hornchurch, both of England

[73] Assignee: May & Baker Ltd., Essex, England

[21] Appl. No.: 262,521

[22] Filed: May 11, 1981

[30] Foreign Application Priority Data

May 13, 1980 [GB] United Kingdom ................ 8015740

[51] Int. Cl.$^3$ .................... A61K 31/445; C07D 211/14
[52] U.S. Cl. ..................................... 424/267; 546/184; 546/192
[58] Field of Search ......................... 546/192; 424/267

[56] References Cited

U.S. PATENT DOCUMENTS 3,156,726 11/1964 Brannock et al. .............. 546/192 X
4,104,383 8/1978 Krausz ............................ 546/192 X

FOREIGN PATENT DOCUMENTS 2283679 4/1976 France.
1055548 1/1967 United Kingdom.

*Primary Examiner*—Richard A. Schwartz
*Attorney, Agent, or Firm*—Stevens, Davis, Miller & Mosher

[57] ABSTRACT

The hitherto unknown phenylpropargylamine derivative 1-(3,5-bistrifluoromethylphenyl)-3-(4-tert-butylpiperidino)prop-1-yne, and acid addition salts thereof, have been found to be useful for killing warm-blooded vermin, especially rodents. Processes for the preparation of the new phenylpropargylamine derivative are described and so are suitable rodenticidal compositions.

14 Claims, No Drawings

RODENTICIDAL 1-(3,5-BISTRIFLUOROMETHYLPHENYL)-3-(4-T-BUTYLPIPERIDINO)PROP-1-YNE

This invention relates to a new useful phenylpropargylamine derivative and acid addition salts thereof, to processes for their preparation, and to compositions containing them suitable for oral ingestion by, and killing of, warm-blooded vermin.

The compounds of the present invention are the phenylpropargylamine derivative of the formula:

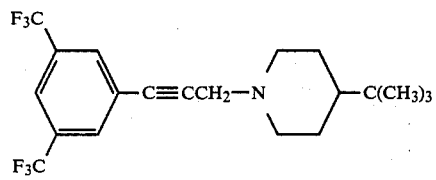

[i.e. 1-(3,5-bistrifluoromethylphenyl)-3-(4-tert-butyl-piperidino)prop-1-yne] and acid addition salts thereof. The acid addition salts may be formed with inorganic acids, for example hydrochloric, sulphuric, phosphoric, nitric or sulphamic acid, or with organic acids, for example acetic, octanoic, methanesulphonic, glutamic or 2-hydroxyethanesulphonic acid.

The compound of formula I and its acid addition salts are highly toxic to warm-blooded animals, more especially rodents, e.g. rats and mice, by oral administration and may be used to kill warm-blooded vermin, i.e. undesired warm-blooded animals, for example to control rodent infestations. Where reference is made in the present specification to the use of the compound of formula I to kill warm-blooded vermin, for example as a rodenticide, it is to be understood that such reference is intended to include also the acid addition salts of the compound of formula I.

The utility of the compound of formula I as a rodenticide is demonstrated by the following tests:

Test 1

Acute Oral Toxicity in Mice (Laboratory Strain)

Groups of mice were dosed orally with graded doses of the test compound in aqueous suspension and observed until there had been no deaths for at least three days. The acute oral LD50, that is to say the dose in mg/kg animal body weight necessary to kill 50% of the mice, was determined from the numbers of animals for each dose which died during the observation period by reference to published tables.

| | LD50 | Observations |
|---|---|---|
| Compound of formula I as hydrochloride salt | 23 | There were no marked signs of poisoning prior to death at between 3 and 9 days after dosing. |
| Compound of formula I as free base | 68 | Some signs of poisoning were seen 1 or 2 days after dosing. Death occurred at from 2 to 4 days after dosing. |

Test 2

Laboratory Feeding Tests on Wild Rodents

Warfarin-resistant rats (*Rattus norvegicus*) and mice (*Mus musculus*) from wild populations were fed, in the laboratory, on a bait consisting of coarse oatmeal (90%), wholemeal flour (5%) and corn oil (5%). After feeding for four days on this bait, it was replaced by a treated bait of the same composition, in which 0.1% by weight of the test compound 1-(3,5-bistrifluoromethylphenyl)-3-(4-tert-butylpiperidino)prop-1-yne hydrochloride had been incorporated. The following results given in Table 1 were observed in the period from the commencement of feeding of the treated bait.

TABLE 1

| Species | Sex | Mortality | Lethal Dose of Test Compound (mg/kg animal body weight) | | Days to Death | |
|---|---|---|---|---|---|---|
| | | | Mean | Range | Mean | Range |
| Rat | male | 5/5 | 122.1 | 102.3 to 150.7 | 7.2 | 6 to 8 |
| | female | 5/5 | 129.7 | 70.6 to 210.0 | 5.8 | 5 to 6 |
| Mouse | male | 5/5 | 606.8 | 345.6 to 866.6 | 6.2 | 6 to 7 |
| | female | 5/5 | 493.8 | 446.4 to 570.0 | 5.8 | 5 to 7 |

Test 3

Laboratory Feeding Tests on Mice in Pens

A bait comprising oatmeal, wholemeal flour and corn oil (plain bait) and a bait of similar composition but incorporating 0.1% by weight of the test compound used in Test 2 hereinbefore described (poisoned bait) were prepared and used in the following tests on mice (*Mus musculus*) housed in pens.

Test 3(a)

The poisoned bait alone was offered to 4 male and 4 female mice. The following results given in Table 2 were observed in the period from the commencement of the feeding of the poisoned bait.

TABLE 2

| Quantity of poisoned bait eaten (g) | | | | Mortality | Days to Death | |
|---|---|---|---|---|---|---|
| Day 1 | Day 2 | Day 3 | Days 4–7 | % | Mean | Range |
| 19.1 | 18.8 | 15.4 | 13.7 | 100 | 5.5 | 5 to 7 |

Test 3(b)

A choice of poisoned and plain bait was offered to groups of mice. The following results given in Table 3 were observed in the period from the commencement of the feeding of the baits.

TABLE 3

| Number of mice in pen | Quantity of poisoned bait eaten (g) | | | Mortality % | Days to Death Range |
|---|---|---|---|---|---|
| | Days 1 to 7 | Days 8 to 14 | Days 15 to 21 | | |
| 16 | 55.0 | 0.5 | 0.0 | 93.8 | 4 to 12 |
| 15 | 43.0 | 1.2 | 0.3 | 93.7 | 4 to 9 |
| 24 | 42.3 | 3.5 | 0.7 | 91.7 | 3 to 28 |
| 16 | 25.7 | 2.0 | 0.3 | 93.8 | 6 to 10 |

Test 4

Laboratory Simulated Field Test on Wild Rats (*Rattus norvegicus*) in confinement One male and nine female rats were given the choice of two feeding points, at each of which the animals were offered a bait consisting of medium oatmeal (95%) and wholemeal flour (5%) (plain bait). After a period of six days during which the plain bait was offered at both feeding points, the plain bait was replaced at one of the feeding points by a bait of the same composition in which 0.1% by weight of the test compound used in Test 2 hereinbefore described had been incorporated (poisoned bait), while the plain bait continued to be offered at the other feeding point. The following results given in Table 4 were observed in the period from six days before (Days -6 to -1) to twelve days (Days 1 to 12) after the commencement of the period during which the poisoned bait was offered.

TABLE 4

| Period before commencement of offering poisoned bait | Quantity of bait eaten (g) | | | Cumulative mortality % |
|---|---|---|---|---|
| | Feeding Point A Plain bait | Feeding Point B Plain bait | Total bait eaten | |
| Day | | | | |
| −6 | 11.0 | 18.9 | 29.9 | — |
| −5 | 51.7 | 42.4 | 94.1 | — |
| −4 | 153.4 | 31.1 | 184.5 | — |
| −3 | 130.7 | 94.1 | 224.8 | — |
| −2 | 112.9 | 81.0 | 193.9 | — |
| −1 | 99.0 | 42.0 | 141.0 | — |

| Period after commencement of offering poisoned bait | Quantity of bait eaten (g) | | | Cumulative mortality % |
|---|---|---|---|---|
| | Feeding Point A Poisoned bait | Feeding Point B Plain bait | Total bait eaten | |
| Day | | | | |
| 1 | 99.7 | 80.1 | 179.8 | — |
| 2 | 95.2 | 65.9 | 161.1 | — |
| 3 | 19.8 | 67.4 | 97.2 | — |
| 4 | 5.1 | 38.1 | 43.2 | 30 |
| 5 | 1.8 | 27.7 | 29.5 | — |
| 6 | — | 19.3 | 19.3 | 60 |
| 7 | — | 4.0 | 4.0 | 70 |
| 8 | — | 6.5 | 6.5 | 80 |
| 9 | 1.3 | 3.7 | 5.0 | 90 |
| 10 | — | — | — | — |
| 11 | 0.7 | 0.7 | 1.4 | — |
| 12 | — | — | — | 100 |

Test 5

Field Tests on Rats (*Rattus norvegicus*)

Field tests were carried out on warfarin-resistant rats on three farms. Baits were prepared from either medium oatmeal or soaked wheat in which was incorporated 0.1% by weight of the test compound used in Test 2 hereinbefore described. 100 g lots of bait were laid wherever rats were observed to be running. The amount of bait eaten per day was determined by weighing and the presence or absence of rats was deduced from the amount of bait eaten and by counting the traces of the presence of rats in patches of dust laid for this purpose. The results obtained are given in the following Table 5 and show that the amount of bait eaten on a daily basis had fallen by the fourth day of the tests by 85 to 97%, in comparison with the amount eaten on the first day of the tests. It was estimated that about 80% of the rats initially present on the farms had been killed by the fourth day of the tests, which is a significantly higher percentage kill than that which is usually obtained over the same period of time when anticoagulant rodenticides are used in a similar fashion.

TABLE 5

| | Amount of bait eaten (g) | | |
|---|---|---|---|
| Day | Farm 1 | Farm 2 | Farm 3 |
| 1 | 2060 | 1455 | 4800 |
| 2 | 440 | 1100 | 2680 |
| 3 | 130 | 730 | 360 |
| 4 | 60 | 210 | 445 |
| 6 | 245 | — | — |
| 7 | 130 | 405 | 565 |
| 8 | 85 | 135 | 205 |
| 9 | 30 | 40 | 185 |
| 10 | 10 | 30 | 65 |
| 11 | 40 | 10 | 15 |
| 14 | 65 | 95 | — |
| 15 | — | 45 | — |
| 16 | — | 0 | — |
| Total number of dead rats observed during test | 44 | 8 | 113 |

'—' = amount consumed not recorded

Test 6

Field Test on Mice (*Mus musculus*)

(1) A non-toxic bait was laid at 3 mouse-infested sites and the amount of bait eaten was determined by weighing. (2) The non-toxic bait was then withdrawn and replaced by a similar bait in which was incorporated 0.1% by weight of the test compound used in Test 2 hereinbefore described (poisoned bait). The amount of poisoned bait which was eaten was similarly determined by weighing over a period of three weeks. (3) The poisoned bait was then withdrawn and replaced by the non-toxic bait and the amount of non-toxic bait which was eaten was also similarly determined by weighing. The results obtained are given in following Table 6, the degree of control being calculated by a comparison of the amounts of non-toxic bait which were eaten during the periods before and after use of the poisoned bait.

TABLE 6

| Site | (1) Amount of non-toxic bait eaten per week before replacement by poisoned bait (g) | (2) Amount of poisoned bait eaten (g) | | | (3) Amount of non-toxic bait eaten per week in period following use of poisoned bait (g) | Estimated Control % |
|---|---|---|---|---|---|---|
| | | Week 1 | Week 2 | Week 3 | | |
| 1 | 912 | 368 | 1 | — | 11 | 98.8 |
| 2 | 897 | 441 | 0 | — | 10 | 98.9 |
| 3 | 1880 | 929 | 115 | 11 | 0 | 100 |

'—' = not determined

The compound of formula I may be prepared by the application or adaptation of known methods for the preparation of phenylpropargylamine derivatives, for example by one of the following processes:

(1) The reaction of a compound of the general formula:

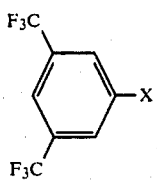

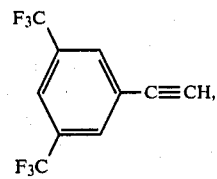

(wherein X represents a halogen, preferably iodine, atom) with the compound of the formula:

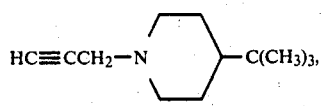

i.e. 4-tert-butyl-1-(prop-2-ynyl)piperidine.

The reaction between a compound of general formula II and the compound of formula III may be effected in the presence of a copper (I) salt, preferably cuprous iodide, and preferably in the presence of a copper (I) salt, preferably cuprous iodide, in the presence of (a) dichlorobis(triphenylphosphine)palladium (II) and, optionally, a triarylphosphine, preferably tri-o-tolylphosphine or triphenylphosphine, or (b) a palladium (II) compound, preferably palladium acetate, and a triarylphosphine, preferably tri-o-tolylphosphine or triphenylphosphine. The reaction may be effected, optionally in the presence of an inert organic solvent, for example acetonitrile, in the presence of an organic base, for example diethylamine, and at a temperature of from ambient temperature to the reflux temperature of the reaction mixture. The organic base may conveniently serve as the solvent in the foregoing process.

(2) The reaction of a compound of the general formula:

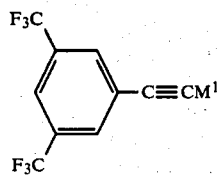

(wherein $M^1$ represents a hydrogen atom or an alkali metal, for example sodium, potassium or lithium, atom or alkaline earth metal, for example magnesium, atom or a copper, silver or zinc atom) with a compound of the general formula:

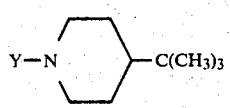

(wherein Y represents a hydrogen atom when the symbol $M^1$ in general formula IV represents a hydrogen atom or Y represents a halogenomethylene, $C_{1-4}$-alkoxy-methylene, chloromercuriomethylene or sulphonyloxymethylene group when the symbol $M^1$ in general formula IV represents a metal atom) and, when the symbol $M^1$ in general formula IV represents a hydrogen atom, i.e. when the compound of general formula IV is of the formula:

a source of formaldehyde.

When the compound of general formula IV is the compound of formula VI, the reaction with the compound of general formula V and the source of formaldehyde, for example paraformaldehyde or formalin, may be effected in the presence of a copper (I) salt, preferably cuprous chloride, in an inert organic solvent, for example dioxan, and at a temperature of from ambient temperature to the reflux temperature of the reaction mixture, preferably 100° C.

When the compound of general formula IV is not the compound of formula VI, the reaction with the compound of general formula V in the absence of a source of formaldehyde may be effected in an inert organic solvent at a temperature of from 0° C. to the reflux temperature of the reaction mixture.

(3) The reaction of a compound of the general formula:

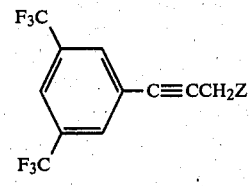

(wherein Z represents a chlorine, bromine or iodine atom or an alkylsulphonyloxy or aryl-sulphonyloxy, for example tosyloxy, radical) with a compound of the general formula:

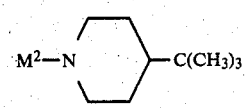

wherein $M^2$ represents an alkali metal, preferably lithium, atom or when the symbol Z in general formula VII represents a chlorine, bromine or iodine atom, $M^2$ may additionally represent a hydrogen atom.

The reaction may be effected in the presence of an inert organic solvent, preferably diethyl ether or tetrahydrofuran when the symbol $M^2$ in general formula VIII represents an alkali metal atom, or for example acetone when the symbol $M^2$ in general formula VIII represents a hydrogen atom.

When the symbol $M^2$ in general formula VIII represents a hydrogen atom, the reaction may be effected in the presence of an inorganic base, for example potassium carbonate, and at a temperature of from ambient temperature to the reflux temperature of the reaction mixture.

The compound of formula III may be prepared by the reaction of the compound of general formula V wherein Y represents a hydrogen atom (viz. 4-tert-butylpiperidine) with 1-bromoprop-2-yne or, conveniently, 1-chloroprop-2-yne in the presence of an inorganic or organic base, for example potassium carbonate or an excess of the compound of general formula V wherein Y represents a hydrogen atom.

The reaction may be effected optionally in the presence of an inert organic solvent, for example methanol, acetone or acetonitrile.

Compounds of general formula VII may be prepared by the application or adaptation of methods described in chemical literature, for example, where Z represents an iodine atom S. Wallat & W. H. Kunau, Chem. Phys. Lipids 13, 159 (1974); where Z represents a bromine atom R. Matchinek & W. Luttke, Synthesis, 1975, 255; and where Z represents a chlorine atom M. J. Murray, J. Amer. Chem. Soc., 60, 2662, (1938).

Acid addition salts may be prepared from the compound of formula I by methods known per se, for example by reaction of stoichiometric quantities of the compound of formula I and the appropriate acid, e.g. an inorganic acid such as hydrochloric, sulphuric, phosphoric, nitric or sulphamic acid, or an organic acid such as acetic, octanoic, methanesulphonic, glutamic or 2-hydroxyethanesulphonic acid, in a suitable solvent, e.g. diethyl ether, ethyl acetate or acetone. The acid addition salts may be purified by recrystallization from one or two or more suitable solvents. Acid addition salt formation provides a means of obtaining the compound of formula I in pure form.

Compounds of general formulae II, IV, V and VIII may be prepared by methods known per se.

By the term "methods known per se" as used in the present specification is meant methods heretofore used or described in the chemical literature.

The following Example illustrates the preparation of compounds of the present invention.

EXAMPLE 1

A mixture of 1-(3,5-bistrifluoromethylphenyl)-3-bromoprop-1yne (10.0 g), 4-tert-butylpiperidine (4.6 g) and finely ground anhydrous potassium carbonate (15.0 g) in anhydrous acetone (150 ml) was stirred at ambient temperature for 48 hours, then filtered and the solvent was removed under reduced pressure (water-pump). To an ice-cold, stirred solution of the resulting residual oil (compound of formula I) in anhydrous diethyl ether was added a slight excess of hydrogen chloride dissolved in anhydrous diethyl ether. The resulting white precipitate was filtered off, washed with diethyl ether and dried under high vacuum to give 1-(3,5-bistrifluoromethylphenyl)-3-(4-tert-butylpiperidino)prop-1-yne hydrochloride (10.95 g), m.p. 201°–202° C.

4-Tert-butylpiperidine used in the foregoing example can be made by the method described in U.S. Pat. No. 3,101,340 (Chem. Abs. 67, 59294k).

The residual oil prepared as described above had an elementary analysis of C: 61.6%; H: 6.1%; N: 3.7%.

The molecular formula for 1-(3,5-bistrifluoromethylphenyl)-3-(4-tert-butylpiperidino)prop-1-yne (compound of formula I) $C_{20}H_{23}F_6N$ requires C: 61.4%; H: 5.9%; N: 3.6%.

EXAMPLE 2

A mixture of 1-(3,5-bistrifluoromethylphenyl)-3-bromoprop-1-yne (173.1 g), 4-tert-butylpiperidine (73.9 g) and finely ground anhydrous potassium carbonate (262.3 g) in anhydrous acetone (2.5 liters) was stirred at ambient temperature for 41 hours, then filtered and the solvent was removed under reduced pressure (water-pump). To an ice-cold, stirred solution of the resulting residual oil in anhydrous diethyl ether (1.5 liters) there was added a slight excess of hydrogen chloride dissolved in anhydrous diethyl ether. The resulting white precipitate was filtered off, washed with diethyl ether and dried under high vacuum to give 1-(3,5-bistrifluoromethylphenyl)-3-(4-tert-butylpiperidino)prop-1-yne hydrochloride (191.3 g), m.p. 213°–214° C.

1-(3,5-bistrifluoromethylphenyl)-3-bromoprop-1-yne, used as a starting material in the above preparation, may be prepared as follows:

To a stirred solution of 3,5-bistrifluoromethyliodobenzene (which may be prepared as described by S. D. Ross et al, J. Amer. Chem. Soc. (1953), 75, 4967–4969; 340.1 g) in anhydrous diethylamine (665 ml), cooled to 10° C. and under an inert atmosphere, there were added successively copper (I) iodide (1.81 g) and dichlorobis(triphenylphosphine)palladium (3.51 g). 2-Propyn-1-ol (57.8 g) was then added dropwise over 20 minutes and the reaction mixture was then maintained, with stirring, at 25° to 30° C. for 4 hours. The reaction mixture was then maintained overnight, with stirring, at ambient temperature. The solvent was removed by evaporation under reduced pressure (water-pump) and the crystalline residue was partitioned between diethyl ether (670 ml) and water (200 ml). The ether layer was separated, washed with water (2×200 ml), dried over anhydrous sodium sulphate and evaporated under reduced pressure (water-pump). The solid residue thus obtained was distilled to give 1-(3,5-bistrifluoromethylphenyl)-prop-1-yn-3-ol, in the form of a white crystalline solid (231.7 g), m.p. 58°–60° C., b.p. 87°–91° C./1 mm Hg.

Bromine (139.7 g) was added dropwise over 45 minutes to a stirred suspension, cooled to 0° C., of triphenylphosphine (229.2 g) in anhydrous acetonitrile (843 ml) under an inert atmosphere. After one hour, the cooling bath was removed and a solution of 1-(3,5-bistrifluoromethylphenyl)-prop-1-yn-3-ol (231.7 g) in anhydrous acetonitrile (408 ml) was added dropwise to the reaction mixture over 45 minutes. The reaction mixture was then stirred at ambient temperature for 2 hours, filtered and the filtrate evaporated under reduced pressure (water-pump). The residual oil was extracted with diethyl ether (1 liter) and the ethereal extract was treated with decolourizing charcoal, filtered and evaporated under reduced pressure (water-pump). The residual oil thus obtained was distilled to give 1-(3,5-bistrifluoromethylphenyl)-3-bromoprop-1-yne (260.8 g), b.p. 54°–57° C/0.05–0.02 mm Hg.

EXAMPLE 3

Copper (I) iodide (0.03 g), dichlorobis(triphenylphosphine)palladium (0.05 g), 4-tert-butyl-1-(prop-2-ynyl)-piperidine (2.69 g) and anhydrous diethylamine (20 ml) were added successively, under an inert atmosphere, to 3,5-bistrifluoromethyliodobenzene (5.1 g) and the reaction mixture was then stirred at ambient temperature for 48 hours. The solvent was then evaporated under reduced pressure (water-pump) and the residue was extracted with diethyl ether (4×100 ml). The combined ethereal extracts were treated with decolourizing charcoal, filtered and a slight excess of a saturated solution of hydrogen chloride in anhydrous diethyl ether was added to the filtrate, with stirring. The resulting suspension was filtered and the residue was washed with diethyl ether and dried under vacuum, to give 1-(3,5-bistrifluoromethyl)-3-(4-tert-butylpiperidino)prop-1-yne hydrochloride, (5.1 g), m.p. 215°–216° C. after recrystallisation from ethanol.

4-tert-Butyl-1-(prop-2-ynyl)piperidine used as a starting material in the above preparation may be prepared as follows:

Anhydrous potassium carbonate (196 g) was added to a solution of 4-tert-butylpiperidine (98.9 g) in anhydrous acetone (1.2 liters) and the resulting suspension was cooled to 0° C., with stirring under an inert atmosphere. A solution of 1-bromoprop-2-yne (87.5 g) in anhydrous acetone (100 ml) was then added dropwise, the temperature being maintained below 5° C. The reaction mixture was then stirred at ambient temperature for 24 hours, filtered and the filtrate was evaporated under reduced pressure (water-pump). The residual oil thus obtained was extracted with petroleum spirit (b.p. 40°–60° C.). The resulting solution was treated with decolourizing charcoal, filtered and the filtrate was evaporated to give 4-tert-butyl-1-(prop-2-ynyl)piperidine (105 g), m.p. 48°–49° C., which may be further purified by distillation under reduced pressure (water-pump) (b.p. 108°–110° C./15 mm Hg) or by sublimation under reduced pressure (water-pump) at 80° C./20 mm Hg.

4-tert-Butyl-1-(prop-2-ynyl)piperidine may also be prepared by the procedure described above but replacing the 1-bromoprop-2-yne by the appropriate equivalent amount of 1-chloroprop-2-yne.

EXAMPLE 4

4-tert-Butyl-1-(prop-2-ynyl)piperidine (prepared as described in Example 3; 37.3 g) and anhydrous diethylamine (800 ml) were added to 3,5-bistrifluoromethylbromobenzene [which may be prepared as described by E. T. McBee et al, J. Amer. Chem. Soc. (1950), 72, 1651; 61.0 g] and dichlorobis(triphenylphosphine)palladium (0.26 g), copper (I) iodide (0.26 g) and triphenylphosphine (0.26 g) were added with stirring, under an inert atmosphere, to the solution thus obtained. The reaction mixture was heated under reflux for 17 hours and then cooled and filtered. The filtrate was evaporated under reduced pressure (water-pump) and the residual oil thus obtained was dissolved in diethyl ether. A slight excess of a saturated solution of hydrogen chloride in anhydrous diethyl ether was then added, with stirring, to the ethereal solution. The resulting suspension was filtered and the solid residue was washed with diethyl ether and dried under vacuum, to give solid 1-(3,5-bistrifluoromethylphenyl)-3-(4-tert-butylpiperidino)prop-1-yne hydrochloride (72 g), which was then partitioned between a small excess of 2 N aqueous sodium hydroxide solution and diethyl ether. The ethereal layer was dried over anhydrous sodium sulphate and evaporated, to give 1-(3,5-bistrifluoromethylphenyl)-3-(4-tert-butylpiperidino)prop-1-yne in the form of an oil, which had the elementary analysis C: 61.7%; H: 5.8%; N: 3.5% ($C_{20}H_{23}F_6N$ requires C: 61.4%; H: 5.9%; N: 3.6%).

EXAMPLE 5

A solution of 1-(3,5-bistrifluoromethylphenyl)-3-(4-tert-butylpiperidino)prop-1-yne (9.78 g) in anhydrous diethyl ether (12.5 ml) was treated with a solution of methanesulphonic acid (2.40 g) in anhydrous diethyl ether (12.5 ml), stirred and cooled. The solid precipitate was removed by filtration, washed with cold anhydrous diethyl ether and dried at 0.05 mm Hg for 2 hours, to give 1-(3,5-bistrifluoromethylphenyl)-3-(4-tert-butylpiperidino)prop-1-yne methanesulphonate (11.61 g), m.p. 164°–165° C., in the form of a white powder which had the elementary analysis C: 51.3%; H: 5.49%; N: 2.60% ($C_{21}H_{27}F_6NO_3S$ requires C: 51.73%; H: 5.58%; N: 2.87%).

EXAMPLE 6

A solution of 1-(3,5-bistrifluoromethylphenyl)-3-(4-tert-butylpiperidino)prop-1-yne (6.1 g) in ethyl acetate (20 ml) was treated with 2-hydroxyethanesulphonic acid (2.19 g) in ethyl acetate (20 ml). Evaporation of the solvent gave a waxy solid, m.p. 107°–109° C., which was recrystallised from a mixture of ethyl acetate and diethyl ether to give 1-(3,5-bistrifluoromethylphenyl)-3-(4-tert-butylpiperidino)prop-1-yne 2-hydroxyethanesulphonate (containing 0.23 mole of water of crystallization) (5.61 g), m.p. 118°–119° C., in the form of a white crystalline solid which had the elementary analysis C: 50.3%; H: 6.05%; N: 2.68%; $H_2O$: 0.8% ($C_{22}H_{29}F_6NO_4S$. 0.23 $H_2O$ requires C: 50.64%; H: 5.65%; N: 2.68%; $H_2O$: 0.8%).

EXAMPLE 7

1-(3,5-Bistrifluoromethylphenyl)-3-(4-tert-butylpiperidino)prop-1-yne (0.98 g) was treated with dilute nitric acid (0.2446 molar solution; 10.22 ml) and acetone (15 ml) and the solution was immediately evaporated to dryness under reduced pressure (water-pump) at a temperature not greater than 30° C. The white solid thus obtained was dried over phosphorus pentoxide at a pressure of 0.001 mm Hg for 16 hours to give 1-(3,5-bistrifluorophenyl)-3-(4-tert-butylpiperidino)-prop-1-yne nitrate (1.15 g), m.p. 151° C. (with decomposition), which had the elementary analysis C: 52.8%; H: 5.29%; N: 6.22% ($C_{20}H_{24}F_6N_2O_3$ requires C: 52.86%; H: 5.32%; N: 6.16%).

EXAMPLE 8

A stirred solution of 1-(3,5-bistrifluoromethylphenyl)-3-(4-tert-butylpiperidino)prop-1-yne (0.98 g) in anhydrous diethyl ether (50 ml) was treated with a solution of sulphuric acid (e.g. 1.84) in anhydrous diethyl ether (0.25 molar solution; 10 ml). The mixture was allowed to stand for 30 minutes and then filtered. The solid residue was washed with anhydrous diethyl ether (2×20 ml) and dried over phosphorus pentoxide at a pressure of 0.01 mg Hg for 48 hours, to give 1-(3,5-bistrifluoromethylphenyl)-3-(4-tert-butylpiperidino)-prop-1-yne hydrogensulphate (1.15 g), m.p. 221°–222° C. in the form of a white powder which had the elementary analysis C: 49.1%; H: 5.02%; N: 2.76% ($C_{20}H_{25}F_6NO_4S$ requires C: 49.07%; H: 5.15%; N: 2.86%).

According to a feature of the present invention, there is provided a method for killing undesired warm-blooded vermin, more particularly rodents, which comprises the oral administration to the animal of an effective lethal amount of the compound of formula I or acid addition salt thereof, more especially for the purpose of controlling or eradicating infestations of rodents, for example rats and mice, e.g. *Rattus rattus, Rattus norvegicus* and *Mus musculus*. Oral administration to the undesired animal of an effective lethal amount of the compound of formula I or acid addition salt thereof may be achieved by the administration of a single large dose of the compound of formula I or acid addition salt thereof (acute dosing) or, preferably, by the administration of several smaller doses (chronic dosing). When using the compound of formula I or acid addition salt thereof to kill undesired warm-blooded vermin, e.g. rodents, the usual standards of care should be applied in avoiding accidental administration to man and domestic animals and wild animals which it is not desired to control or eradicate.

A particularly valuable property of the compound of formula I and its acid addition salts, especially when used as a rodenticide, is that there is a period of delay, usually about 2 to 9 days, between ingestion and the appearance of symptoms of poisoning and death, during which further amounts may be ingested to lethality during chronic dosing and during which the rodent can leave the vicinity of the place at which ingestion has taken place or the infested area, thereby reducing the risk of suspicion and avoidance of the source of ingestion arising amongst treated and untreated animals.

A further particularly valuable property of the compound of formula I and its acid addition salts is that sedation is the major symptom of toxicity and the treated animals die quietly, without exhibiting signs of distress. Although there is a period of delay between ingestion and death, this period is shorter than that experienced with the anticoagulant rodenticides and permits an advantageous reduction in the period of treatment and observation which is necessary to ensure that satisfactory control of an infestation of warmblooded vermin, particularly rodents, has been achieved.

Anticoagulant rodenticides, for example those of the coumarin type, e.g. warfarin, and those of the indandione type, e.g. chlorophacinone, have been used widely to control or eradicate infestations of rodents, but the appearance in many areas of strains of rodents, particularly rats and mice, which are resistant to anticoagulant rodenticides places increasing limitations on the effectiveness of these anticoagulant rodenticides. The compound of formula I and its acid addition salts have been found to be equally as toxic to strains of rodents which are resistant to anticoagulant rodenticides as to strains of rodents which do not possess this resistance. Accordingly, there is provided, as a preferred feature of the present invention, a method for killing rodents, in particular rats and mice, e.g. *Rattus rattus, Rattus norvegicus* and *Mus musculus,* which are resistant to anticoagulant rodenticides, which comprises the oral administration to those rodents of an effective lethal amount of the compound of formula I or acid addition salt thereof. An effective lethal amount of the compound of formula I and acid addition salts thereof may, if desired, be administered in undiluted form to the warm-blooded vermin, e.g. rodent, which it is desired to kill, but is more usually administered in the form of liquid or solid orally ingestible compositions, for example toxic baits, comprising the compound of general formula I or acid addition salt thereof incorporated in or on a suitable ingestible carrier, for example cereals, e.g. vegetable meals, such as oatmeal, flour, e.g. wheat flour, corn starch, bread, cake, grain, seed, fruit, chocolate, animal meal, animal or vegetable oils and fats, e.g. groundnut oil and corn oil, and other known ingestible animal or vegetable materials, e.g. fish and prepared animal food, with or without ingestible additives, for example attractant flavouring substances, binders, antioxidants, surface active agents, e.g wetting, dispersing or emulsifying agents, and warning colouring substances. Chocolate may be used as a particularly suitable ingestible carrier, either alone or with other ingestible carriers, and sugar may be advantageously used with other ingestible carriers to encourage feeding. Toxic baits may take the natural physical form of the ingestible carrier which is used, e.g. liquids and powders, or may, if desired, be prepared as granules, pills, pellets, tablets or pastes. Toxic baits in liquid, solid or paste form may, if desired, be placed in sachets which may be readily opened by the vermin, e.g. rodents. Toxic baits of suitable physical form, e.g. solid ingestible carriers, e.g. vegetable meal or flour, containing from 2 to 20% of sugar and/or a vegetable or animal oil, or chocolate, may, if desired, be coated on or impregnated into supports comprising small pieces of suitable inert materials, for example blocks or sheets, of wax, wood, synthetic plastics, cardboard or paper, chocolate being a particularly suitable material for coating onto such supports.

Particularly suitable rodenticidal baits comprise from 0.001 to 10% by weight of 1-(3,5-bistrifluoromethylphenyl)-3-(4-tert-butylpiperidino)prop-1-yne or acid addition salt thereof, from 85 to 99.009% by weight of cereal carrier, from 1 to 5% by weight of a vegetable or animal oil and from 0 to 0.05% by weight of a warning colouring substance.

Orally ingestible compositions according to the present invention may also comprise the compound of formula I or acid addition salt thereof in association with solid ingestible carriers which are powders, e.g. powdered talc, which may be used as tracking powders. Such tracking powders may be placed in places, particularly runways, habitually frequented and used by rodents, where they adhere to the fur and feet of the rodents and are subsequently ingested orally during grooming.

Liquid and solid orally ingestible compositions according to the present invention preferably comprise 0.001% to 10%, and more especially from 0.05% to 0.2%, by weight of the compound of formula I or acid addition salt thereof, and may be prepared by incorporating the compound of formula I or acid addition salt thereof in undiluted form in or on liquid or solid ingestible carriers or supports, but are preferably prepared by the incorporation in or on ingestible carriers or supports of liquid or solid concentrates containing the compound of formula I or acid addition salt thereof. Incorporation of the compound of formula I or acid addition salt thereof in undiluted form or in the form of liquid or solid concentrates, in or on ingestible carriers or supports may be achieved by conventional techniques, such as mixing or blending or the incorporation of a solution and removal of the solvent, e.g. by evaporation.

Liquid or solid orally ingestible compositions comprising the compound of formula I or acid addition salt thereof incorporated in or on a suitable orally ingestible carrier or support, form a further feature of the present invention and may, in carrying out the method of the present invention, be suitably distributed at loci of vermin infestation.

The method of the present invention may be used, in particular, to protect crop-growing areas, for example cereal crop-growing areas and plantations, e.g. oil-palm plantations, and domestic, agricultural, industrial, commercial and office buildings, for example factories, hospitals, public buildings, storage warehouses, shops, catering establishments and dockyards, and areas in the vicinity of such buildings, and ships against damage by vermin, in particular rodents, e.g. rats and mice.

By the term 'orally ingestible compositions' is meant compositions which are capable of oral ingestion by warm-blooded vermin, e.g. rodents, which are not repellant to aforesaid vermin and which, after ingestion, release lethal amounts of the compound of formula I or acid addition salt thereof into the body of the animal. Suitable orally ingestible carriers and supports will possess properties appropriate to the formation of such orally ingestible compositions and will be chemically and physically compatible with the compound of formula I or acid addition salts thereof.

Liquid or solid concentrates suitable for use in the preparation of liquid or solid orally ingestible compositions according to the present invention comprising the compound of formula I or acid addition salt thereof in association with suitable liquid or solid diluents or carriers, for example solutions, emulsions, syrups, pastes, granules, tablets, pellets or powders, with or without ingestible additives, for example as hereinbefore described, form a further feature of the present invention. Suitable diluents for use in concentrates are liquids or solids which are compatible with the compound of formula I and its acid addition salts and the ingestible carrier or support and which do not adversely affect the acceptability of the ingestible carrier or support to the animal or which, in the case of liquid diluents, may be readily removed, e.g. by evaporation, after incorporation of the liquid concentrates in or on the ingestible carrier or support. Suitable solid diluents for use in concentrates according to the present invention include starch, sucrose, lactose, and edible carriers as hereinbefore described. Suitable liquid diluents for use in concentrates according to the present invention include water and animal or vegetable oils and organic solvents, e.g. xylene, isophorone, dioxan or acetone. Liquid concentrates comprising the compound of formula I dissolved in solvents which are compatible with the compound of formula I and the ingestible carrier or support into or onto which the concentrate is to be incorporated and which does not adversely affect the acceptability of the ingestible carrier or support to the animal, e.g. which is non-repellent to rodents, for example arachis oil, corn oil, xylene, isophorone, dioxan and acetone, are particularly suitable, more especially for the preparation of solid orally ingestible concentrates. Liquid concentrates may also take the form of aqueous or aqueous-organic solutions, suspensions and emulsions, for which purpose acid addition salts of the compound of formula I are particularly suitable.

As will be apparent to those skilled in the art, liquid or solid concentrates according to the present invention may be similar in composition to the liquid or solid orally ingestible compositions according to the present invention but containing a higher concentration of the compound of formula I or acid addition salt thereof, and may be diluted with further amounts of suitable ingestible carrier or support to give compositions ready for administration to the animals. Liquid and solid concentrates according to the present invention suitable for incorporation in or on orally ingestible carriers or supports preferably comprise from 1% to 90%, and more especially from 1% to 5%, by weight of the compound of formula I or acid addition salt thereof.

Where reference is made in the present specification to percentages by weight of 1-(3,5-bistrifluoromethylphenyl)-3-(4-tert-butylpiperidino)-prop-1-yne and acid addition salts thereof in orally ingestible compositions and concentrates according to the present invention, it is to be understood that such percentages refer to the 1-(3,5-bistrifluoromethylphenyl)-3-(4-tert-butyl-piperidino)prop-1-yne content of the acid addition salts.

Liquid or solid rodenticidal concentrates and orally ingestible rodenticidal compositions according to the present invention may also contain the compound of formula I or an acid addition salt thereof in association, if desired, with one or more rodenticidally active anticoagulant compounds, for example those of the coumarin type, e.g. warfarin, or those of the indandione type, e.g. chlorophacinone.

The following Examples 9 to 13 illustrate rodenticidal compositions according to the present invention.

EXAMPLE 9

A concentrate is prepared by dissolving 1-(3,5-bistrifluoromethylphenyl)-3-(4-tert-butylpiperidino)prop-1-yne (2 g) in arachis oil (100 ml). This concentrate may be incorporated into an edible bait in amounts of the compound of from 0.001% to 10%, and preferably from 0.05% to 0.2%, by weight of the total weight of the baits, by admixture with cereal, grain, meal, bran, fruit, vegetables or meat. Such orally ingestible compositions are suitable for use in the control of unwanted rodents.

EXAMPLE 10

A rodenticidal composition is prepared by dissolving 1-(3,5-bistrifluoromethylphenyl)-3-(4-tert-butyl-piperidino)prop-1-yne (1.0 g) in acetone (20 ml), and homogeneously impregnating laboratory rat food pellets (1 kg) to give a toxic bait suitable for use in the control of unwanted rodents.

EXAMPLE 11

1-(3,5-Bistrifluoromethylphenyl)-3-(4-tert-butyl-piperidino)prop-1-yne hydrochloride (5 g) is intimately mixed with a mixture of sucrose (100 g), wheat flour (30 g) and corn starch (70 g). This powdered concentrate is used to coat pieces of scrap meat such as beef and pork, in order to produce a bait for use in the control of unwanted rodents.

EXAMPLE 12

A rodenticidal composition is prepared by intimately mixing 1-(3,5-bistrifluoromethylphenyl)-3-(4-tert-butyl-piperidino)prop-1-yne hydrochloride (1.0 g), oatmeal (899 g), wholemeal flour (50 g) and corn oil (50 g) thoroughly in a blender to achieve uniform distribution of the ingredients throughout the mixture, to give a bait suitable for use in the control of unwanted rodents. If desired, 0.05% by weight of a suitable warning colouring substance, e.g. chlorazol sky blue, may be incorporated in this composition.

EXAMPLE 13

1-(3,5-Bistrifluoromethylphenyl)-3-(4-tert-butyl-piperidino)prop-1-yne hydrochloride (1.0 g), damp coarse oatmeal (949 g) and sugar (50 g) are mixed together thoroughly in a blender to achieve uniform distribution of the ingredients throughout the mixture, to give a rodenticidal composition in the form of a bait which may be used to control unwanted rodents. If desired, 0.05% by weight of a suitable warning colouring substance, e.g. chlorazol sky blue, may be incorporated in this composition.

We claim:
1. 1-(3,5-Bistrifluoromethylphenyl)-3-(4-tert-butyl-piperidino)prop-1-yne of the formula:

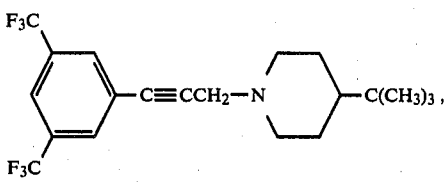

or an acid addition salt thereof.

2. The hydrochloride, sulphate, phosphate, nitrate or sulphamate of the phenylpropargylamine derivative claimed in claim 1.

3. The acetate, octanoate, methanesulphonate, glutamate or 2-hydroxyethanesulphonate of the phenylpropargylamine derivative claimed in claim 1.

4. A method for killing undesired warm-blooded vermin which comprises the oral administration to the animal of an effective lethal amount of the phenylpropargylamine derivative claimed in claim 1 or an acid addition salt thereof.

5. A method according to claim 4 in which the vermin are rodents.

6. A method according to claim 5 in which the rodents are rats or mice.

7. A method according to claim 5 in which the rodents are resistant to anticoagulant rodenticides.

8. A composition for oral ingestion by, and killing of, undesired warm-blooded vermin which comprises an effective lethal amount of the phenylpropargylamine derivative claimed in claim 1, or an acid addition salt thereof, incorporated in or on a carrier or support suitable for ingestion by vermin.

9. A liquid or solid composition according to claim 8 which comprises from 0.001% to 10% by weight of the phenylpropargylamine derivative claimed in claim 1 or an acid addition salt thereof.

10. A liquid or solid composition according to claim 8 which comprises from 0.05% to 0.2% by weight of the phenylpropargylamine derivative claimed in claim 1 or an acid addition salt thereof.

11. A liquid or solid concentrate suitable for incorporation in or on carriers or supports orally ingestible by warm-blooded vermin which comprises from 1% to 90% by weight of the phenylpropargylamine derivative claimed in claim 1 or an acid addition salt thereof.

12. A liquid or solid concentrate suitable for incorporation in or on carriers or supports orally ingestible by warm-blooded vermin which comprises from 1% to 5% by weight of the phenylpropargylamine derivative claimed in claim 1 or an acid addition salt thereof.

13. A composition according to any one of claims 8 to 12 which includes, in addition, one or more rodenticidally active anticoagulant compounds.

14. A composition according to any one of claims 8 to 13 which includes, in addition, a colouring substance as a warning to humans that the compositions are intended only for vermin.

* * * * *